(12) United States Patent
Steiner et al.

(10) Patent No.: US 6,599,410 B1
(45) Date of Patent: Jul. 29, 2003

(54) DEVICE FOR REHYDRATION AND ELECTROPHORESIS OF GEL STRIPS AND METHOD OF USING THE SAME

(75) Inventors: Urs Steiner, Sunnyvale, CA (US); Mohammed Rezaul Islam, Sunnyvale, CA (US); Eric R. Hungerman, Danville, CA (US)

(73) Assignee: Amersham Biosciences (SF) Corp, San Francisco, CA (US)

( * ) Notice: Subject to any disclaimer, the term of this patent is extended or adjusted under 35 U.S.C. 154(b) by 128 days.

(21) Appl. No.: 09/819,061

(22) Filed: Sep. 1, 2000

Related U.S. Application Data

(63) Continuation of application No. 09/095,002, filed on Jun. 9, 1998, now Pat. No. 6,113,766.
(60) Provisional application No. 60/059,810, filed on Sep. 24, 1997, provisional application No. 60/049,135, filed on Jun. 10, 1997, and provisional application No. 60/048,999, filed on Jun. 9, 1997.

(51) Int. Cl.[7] ..................... G01N 27/447; G01N 27/453
(52) U.S. Cl. ....................................... 204/466; 204/616
(58) Field of Search ................................. 204/456, 459, 204/466, 606, 616

(56) References Cited

U.S. PATENT DOCUMENTS

| | | | | |
|---|---|---|---|---|
| 5,747,600 A | * | 5/1998 | Fang | 524/386 |
| 5,785,835 A | * | 7/1998 | Saito et al. | 204/456 |
| 6,113,766 A | * | 9/2000 | Steiner et al. | 204/606 |

* cited by examiner

*Primary Examiner*—Jill Warden
*Assistant Examiner*—Alex Noguerola
(74) *Attorney, Agent, or Firm*—Royal N. Ronning, Jr.

(57) ABSTRACT

The present invention involves a gel strip carrier module for a gel strip that reduces the handling of the gel strip and the hands-on-time during preparation of the gel strip for isoelectric focusing. The gel carrier module includes a gel strip chamber that serves as both a rehydration and focusing chamber, and allows the sample to be applied either throughout the entire gel or in a defined zone. The gel carrier module includes a pair of electrodes near opposite ends of the chamber that the gel strip rests on, gel side facing down. The gel carrier module includes a cover with hold-down blocks or pressure blocks to assure reliable, light contact between the gel and the electrodes during focusing. A rehydration buffer is added into the chamber, and the gel strip is gently placed in the chamber, gel side down, for rehydration. The rehydration buffer may include the sample, or, in the event that the sample needs to be applied after rehydration, the gel carrier module includes sample application wells between the electrodes that the sample can be added to after rehydration of the gel strip.

15 Claims, 7 Drawing Sheets

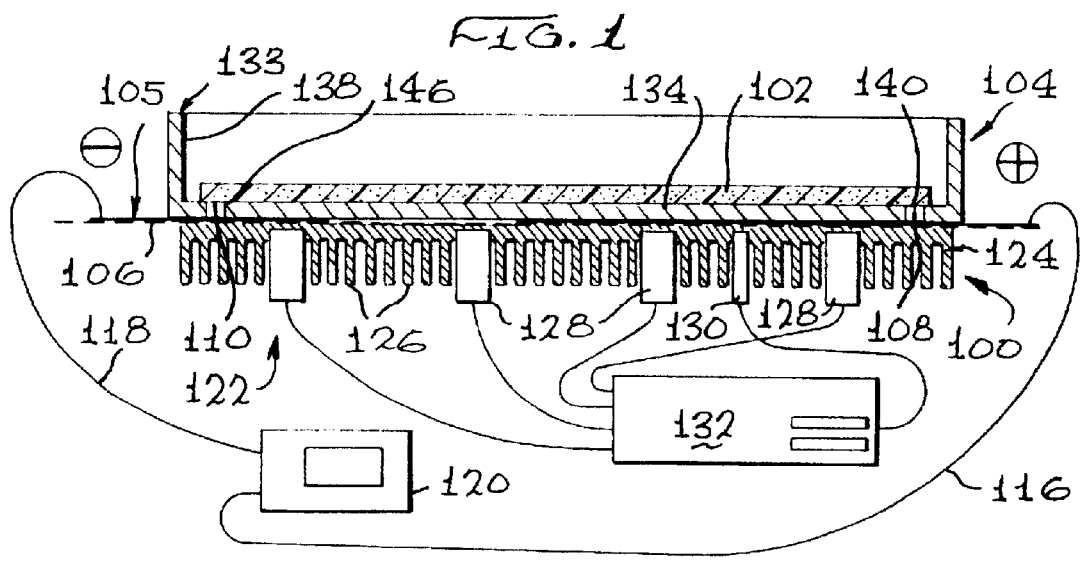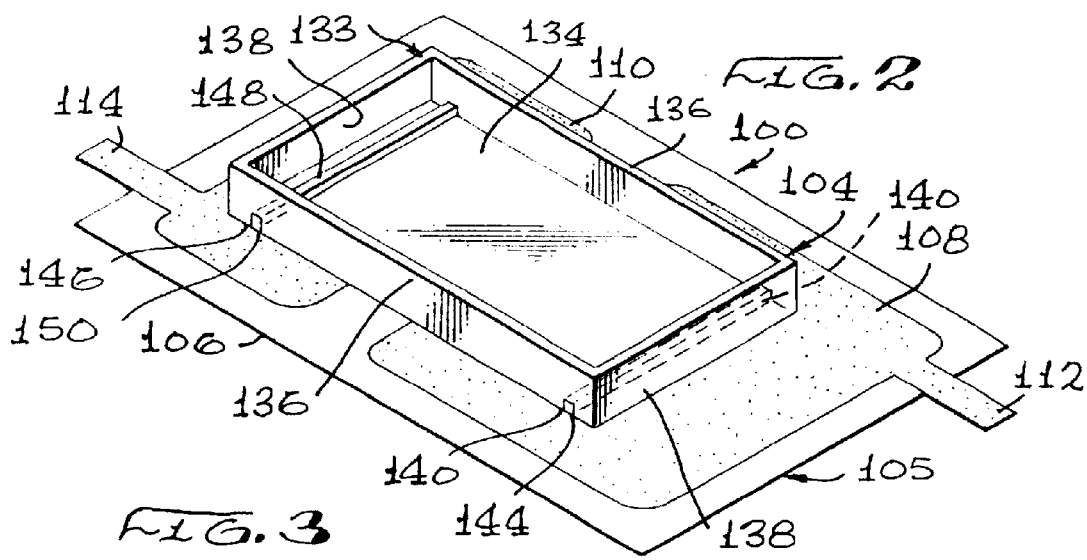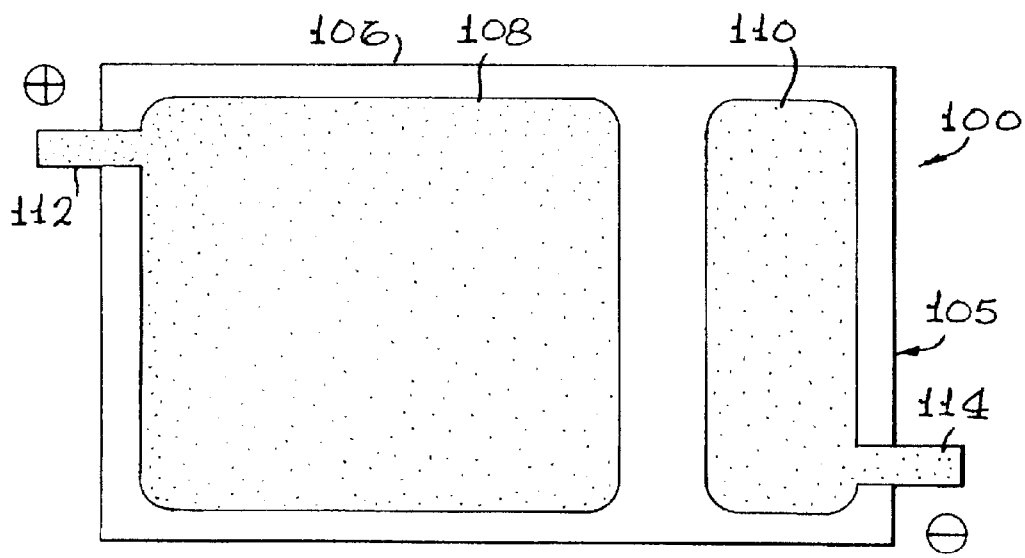

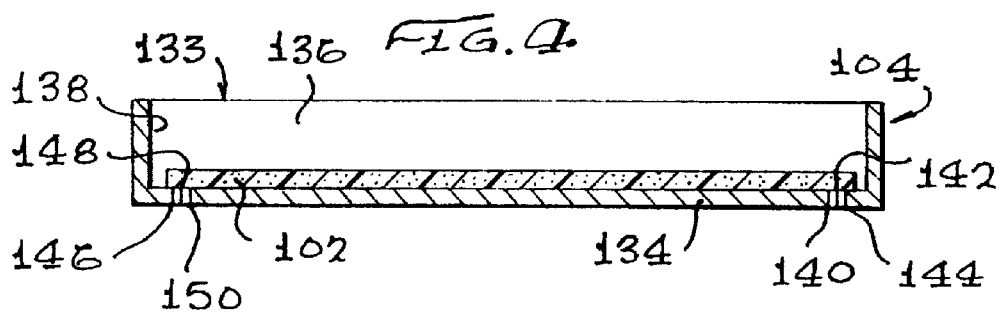
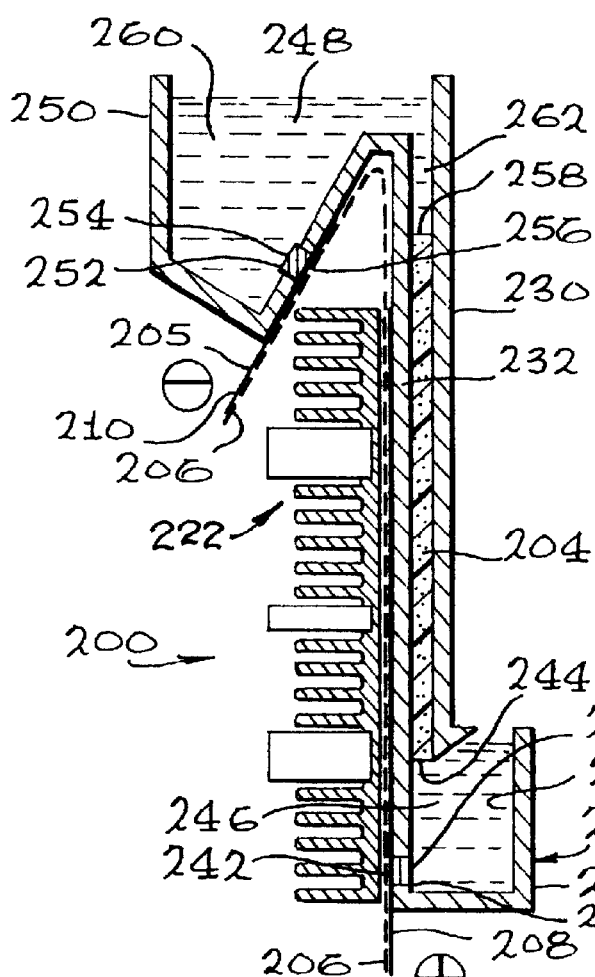
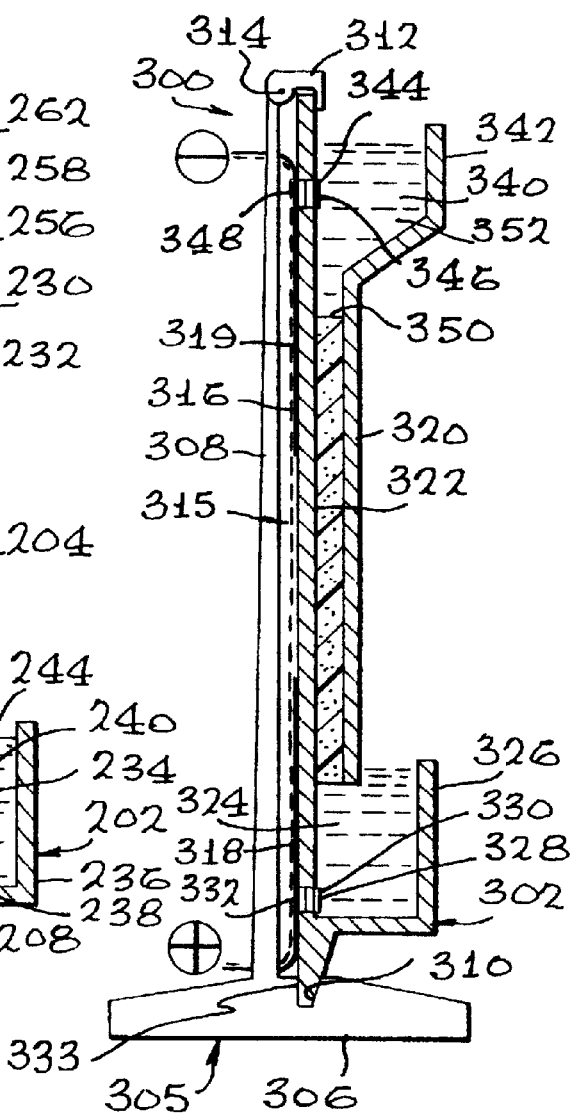

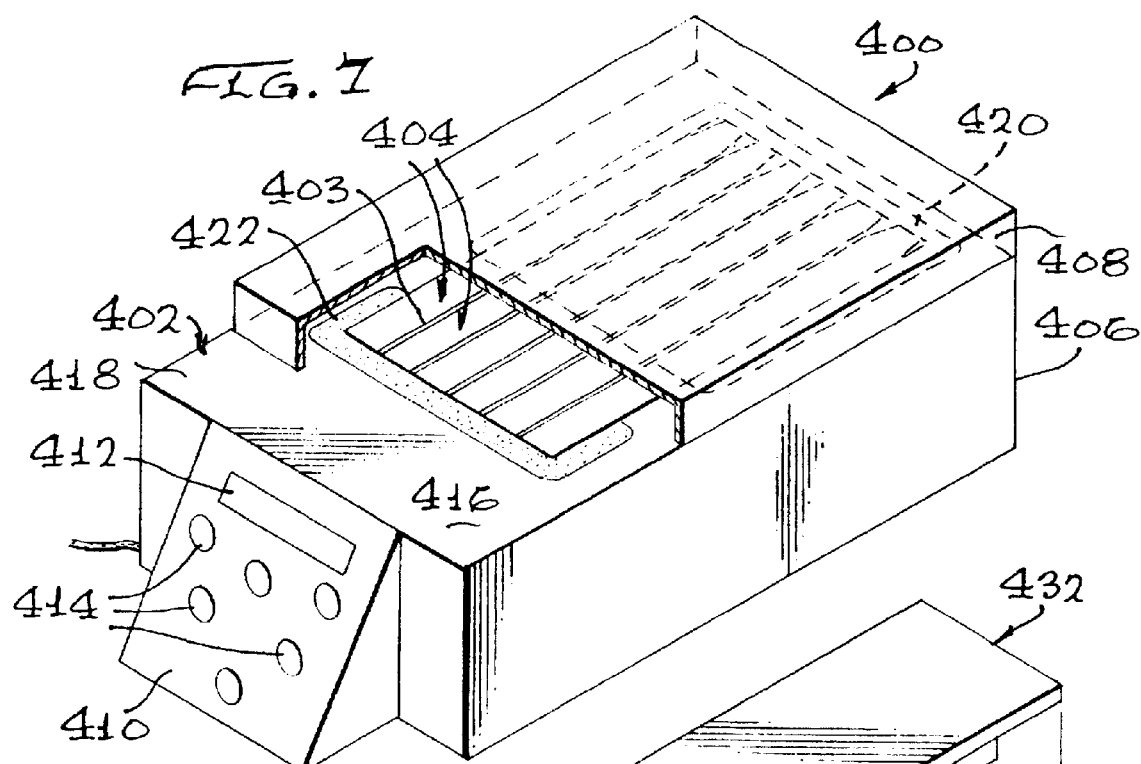
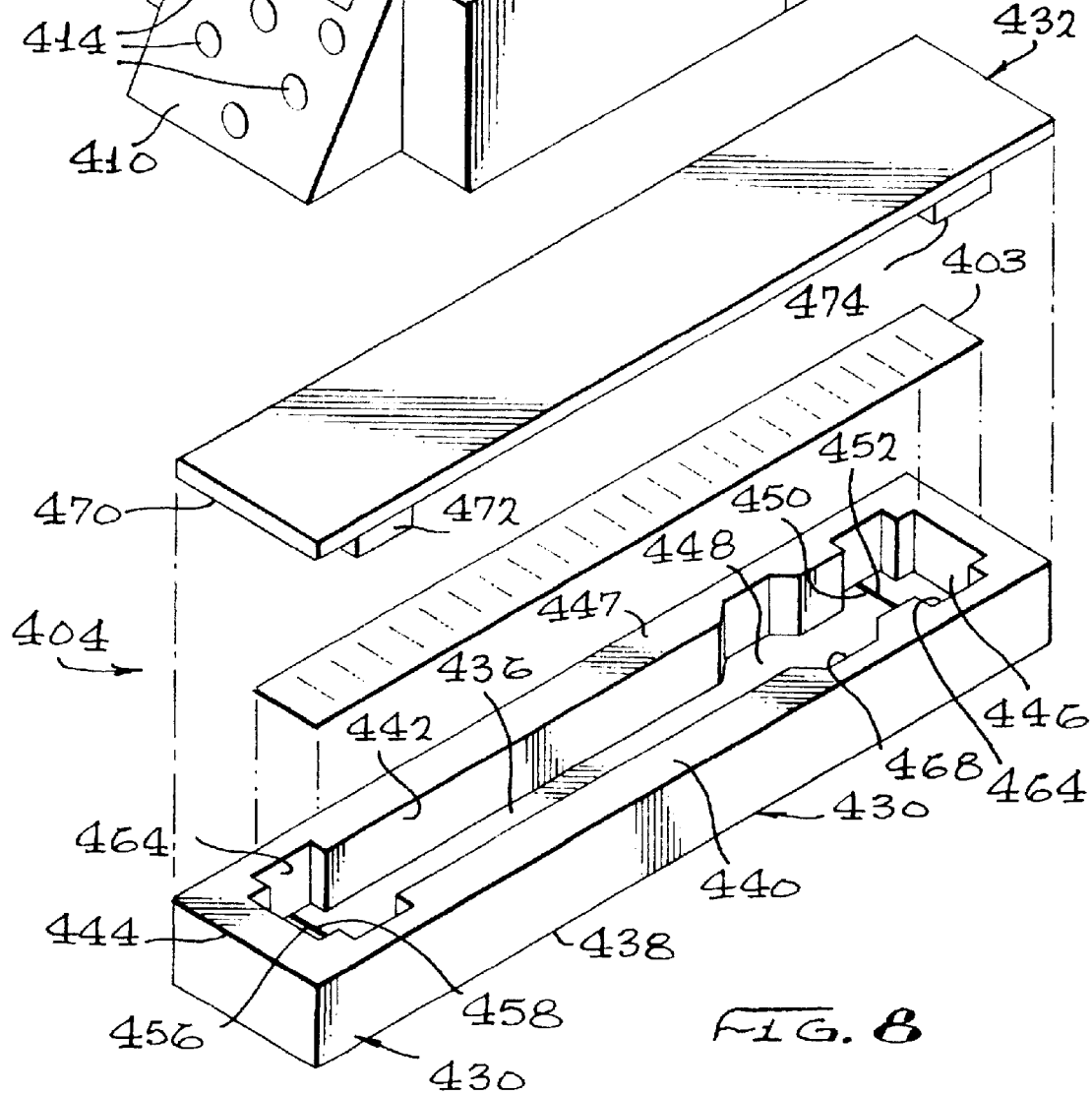

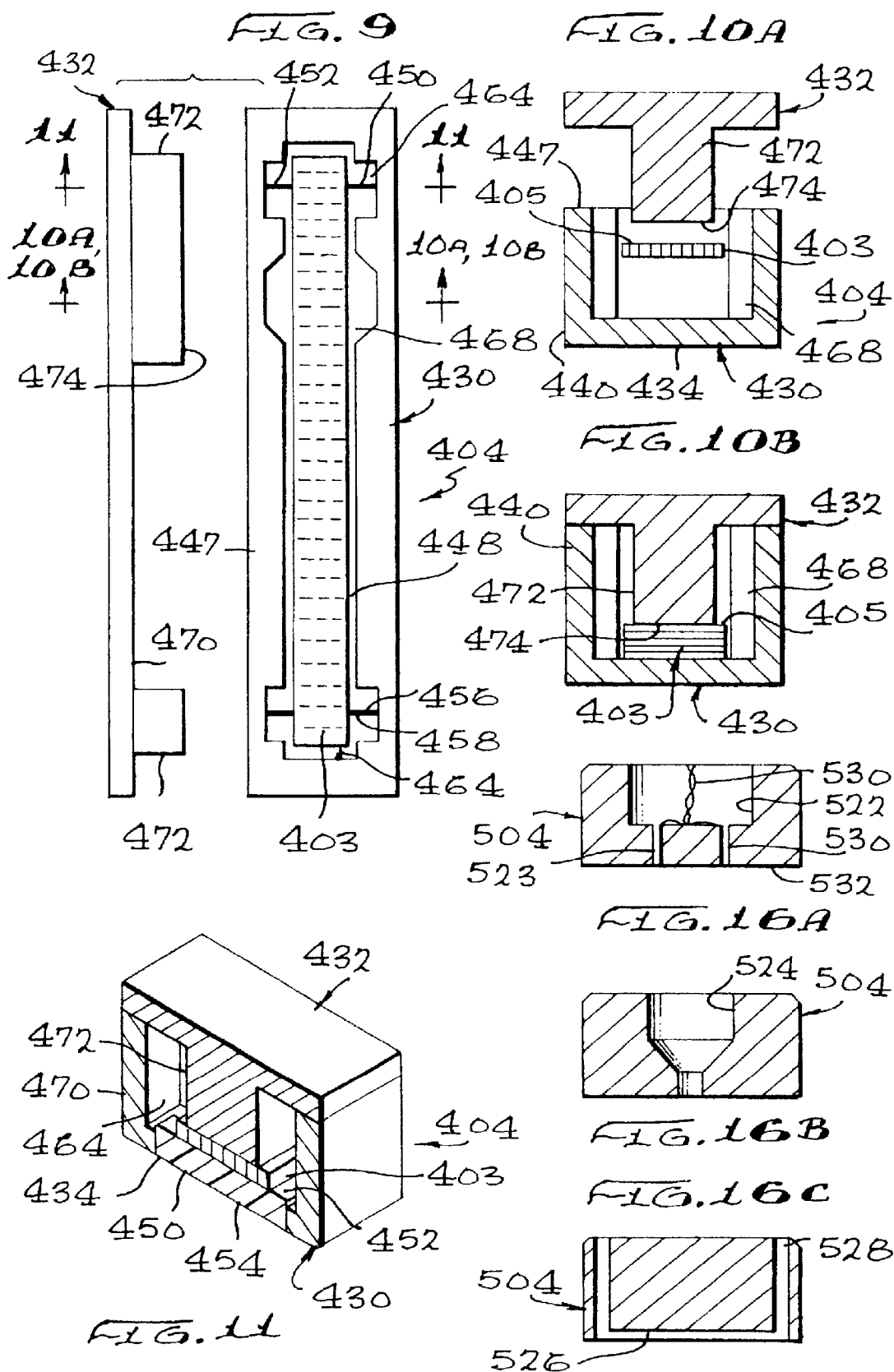

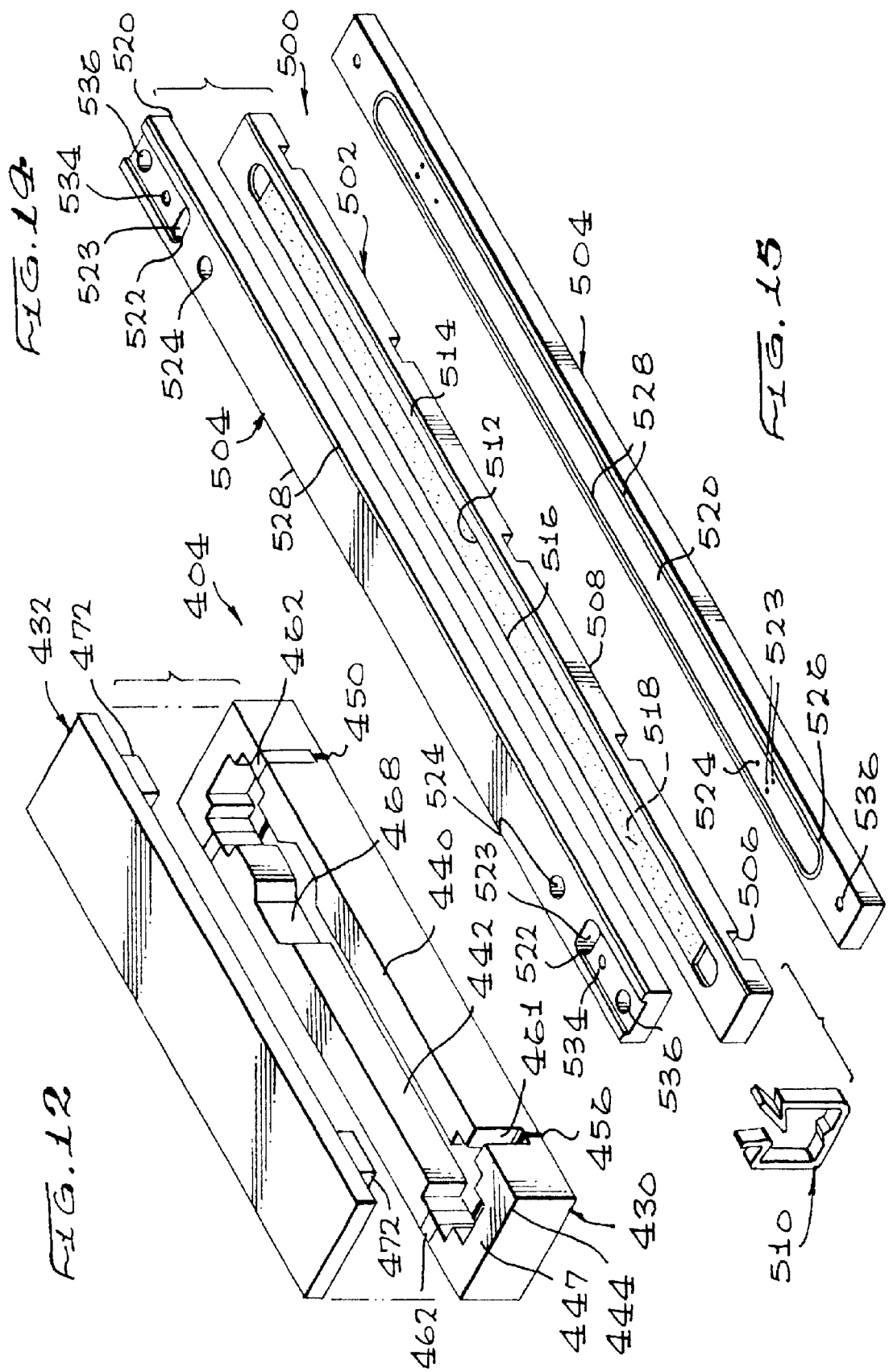

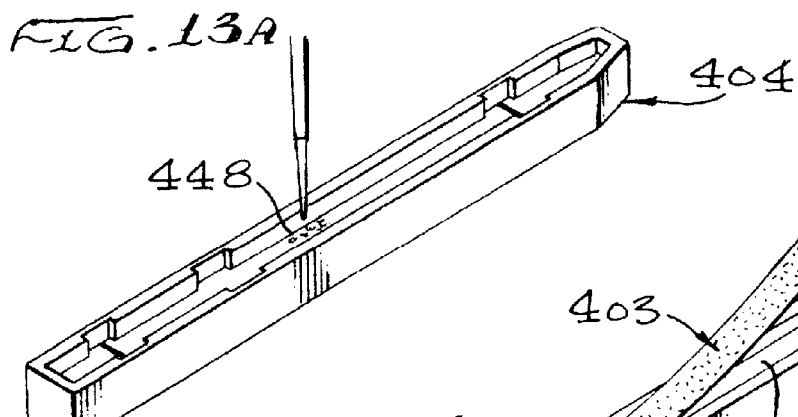
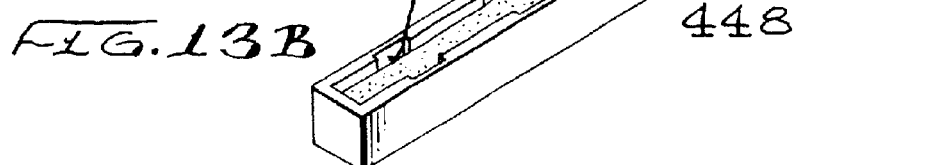
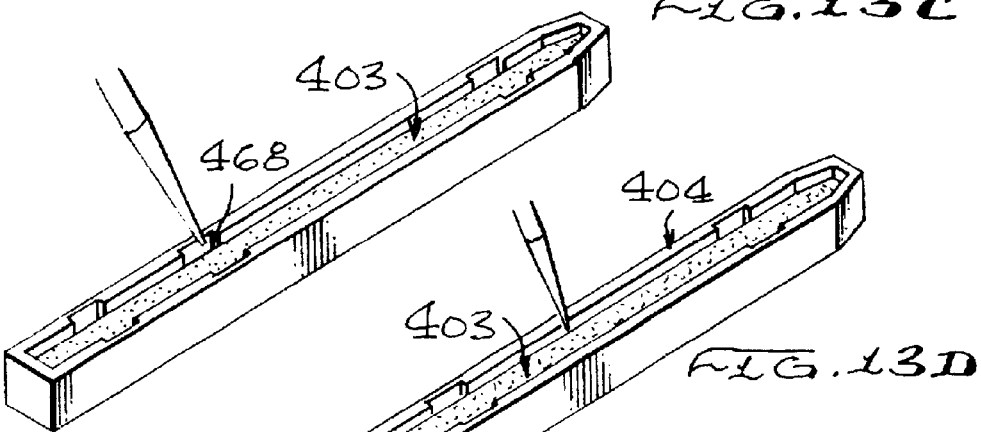
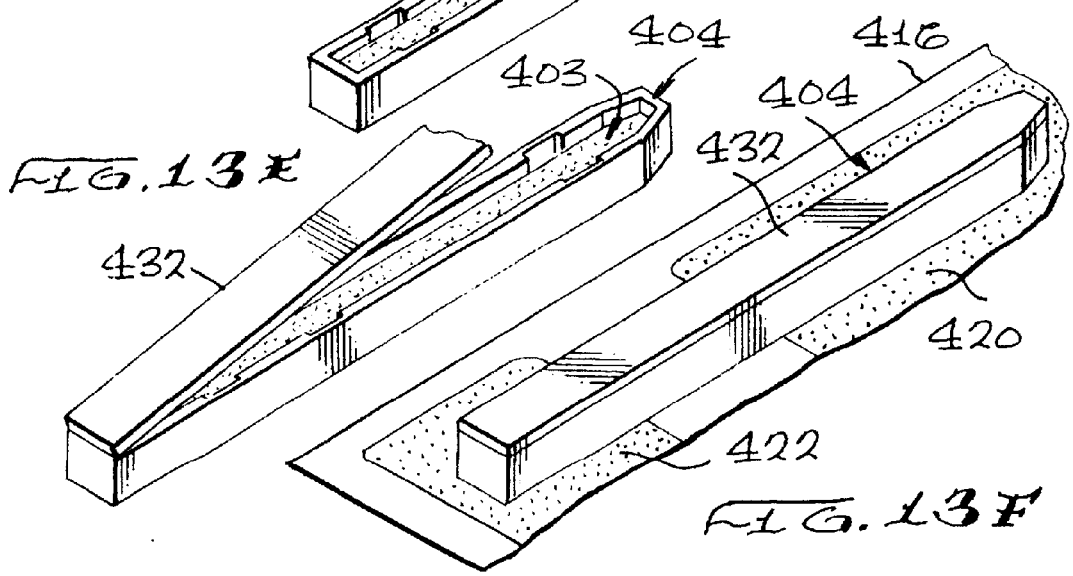

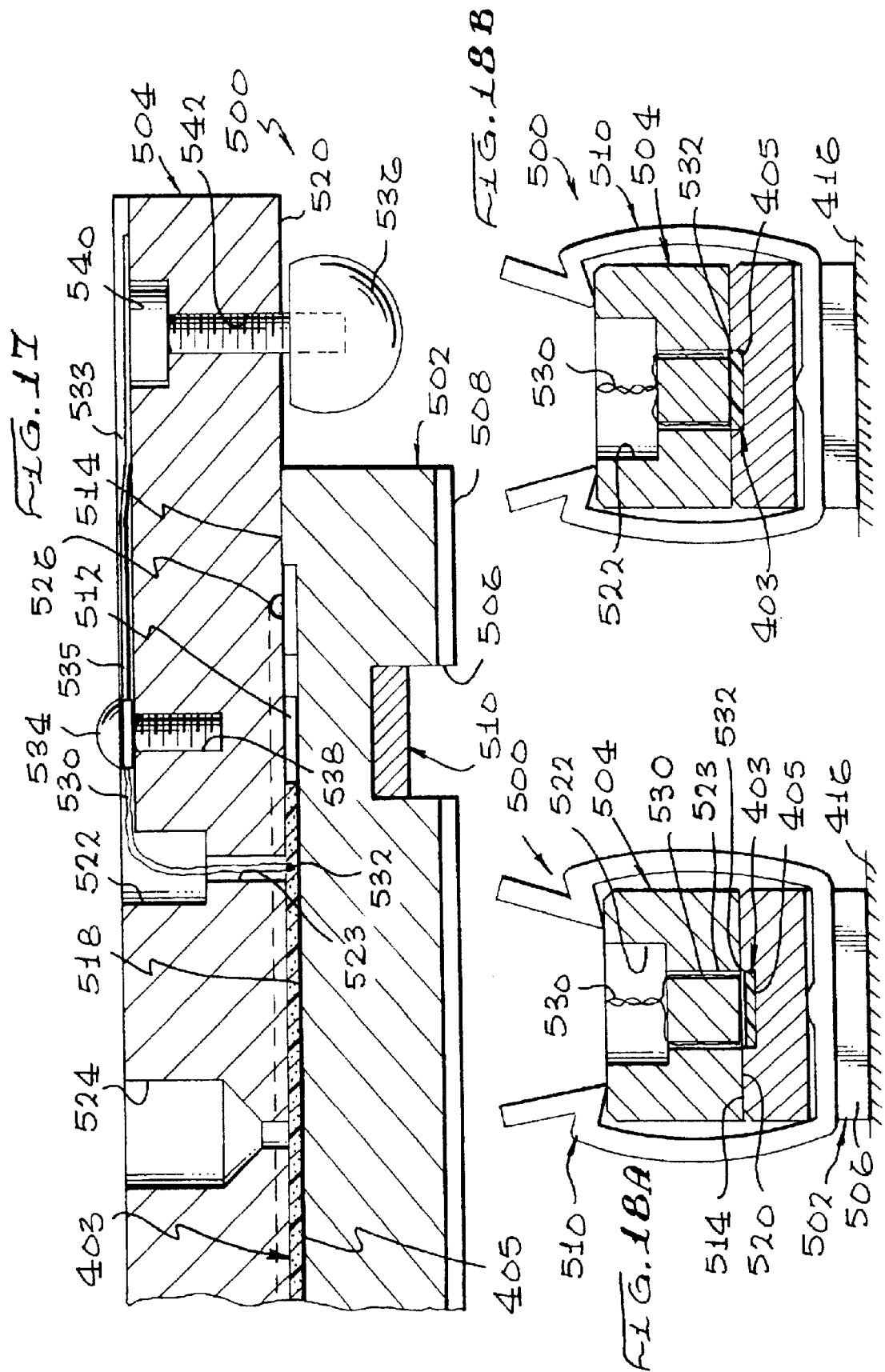

DEVICE FOR REHYDRATION AND ELECTROPHORESIS OF GEL STRIPS AND METHOD OF USING THE SAME

RELATED APPLICATIONS

This application is a continuation of Ser. No. 09/095,002 filed Jun. 9, 1998 now U.S. Pat. No. 6,113,766, which claims the benefit of U.S. Provisional Application Ser. No. 60/048,999, filed on Jun. 9, 1997, No. 60/049,135, filed on Jun. 10, 1997, and No. 60/059,810, filed on Sep. 24, 1997.

FIELD OF THE INVENTION

The invention relates to devices and methods used in preparing gel strips for electrophoresis and performing electrophoresis on gel strips.

BACKGROUND OF THE INVENTION

Two-dimensional electrophoresis is an effective way to analyze complex mixtures of proteins. Typically, two-dimensional electrophoresis involves separating the protein mixture by the intrinsic charge characteristics of the proteins, i.e., their isoelectric points, in a first dimension by a type of electrophoresis called isoelectric focusing, and then separating the protein mixture in a second dimension by electrophoresis. In the second-dimension electrophoresis, a gel strip containing the proteins separated in the first dimension is incubated in a buffer appropriate for the second-dimension electrophoresis, and applied to a second-dimension vertical or horizontal slab gel so that the proteins can be electrophoresed out of the first-dimension gel and into the second gel under appropriate conditions to separate the proteins on the basis of molecular mass.

The first-dimension electrophoresis, i.e., isoelectric focusing, is usually performed on thin flat strips of polyacrylamide gel containing a covalently immobilized pH gradient, i.e., IPG gel strips. The IPG gel strips are commercially available in a dehydrated state and are rehydrated in an appropriate buffer before use. Currently, each IPG gel strip is rehydrated in a first gel carrier apparatus, and then handled and transferred by the user to a second gel carrier apparatus for isoelectric focusing (IEF) to separate the supplied proteins by isoelectric point.

A problem with the present processes and gel carrier apparatuses for IPG gel strip preparation and isoelectric focusing is that the IPG gel strips tend to be fragile, flimsy, and difficult to handle between the steps of rehydration and first dimension electrophoresis, as is commonly practiced at present time. Transferring the gel strip from a first gel carrier apparatus for rehydration to a second gel carrier apparatus for isoelectric focusing requires to much handling and hands-on-time for the first-dimension electrophoresis.

SUMMARY OF THE INVENTION

To this end, a first aspect of the present invention involves a gel strip carrier module for a gel strip that reduces the handling of the gel strip and the hands-on-time during preparation of the gel strip for isoelectric focusing by including a gel strip chamber that serves as both a rehydration and focusing chamber.

A second aspect of the present invention involves a device for rehydrating and performing electrophoresis on a gel strip having two ends and a gel face. The device includes a holder having a gel strip chamber configured to receive the gel strip and a rehydration buffer medium. First and second electrodes are carried by the holder. The electrodes include internal electrical contact points adapted to contact the gel face of the gel strip near the ends of the gel strip and external electrical contact points adapted to be electrical connected to a power supply for performing electrophoresis on the gel strip.

A preferred embodiment of the above aspect of the invention includes a number of features. A first feature is that the internal electrical contact points are carried by the holder and are adapted to contact the face of the gel strip with the gel strip oriented gel face down in the chamber. A second feature is that the holder includes electrolytic gas bubble escape vents comprised of a widened area in the chamber adjacent to an internal electrical contact. A third feature is that the chamber may include an optional sample introduction area between the internal electrical contact points comprised of a widened area in the chamber adjacent to a lateral edge of the gel strip. A fourth feature is that the holder includes a floor and a wall, an inner surface of the wall and upper surface of the floor define the gel strip chamber, the gel strip chamber includes a first end and a second end, the internal electrical contact point of the first electrode is carried by the floor adjacent to the first end of the gel strip chamber, the internal electrical contact point of the second electrode is carried by the floor adjacent to the second end of the gel strip chamber. A sixth feature is that the gel carrier modules includes a cover for the gel strip chamber. A seventh feature is that at least one member is adapted to maintain the gel strip in contact with the electrical contacts, and the at least one member extends from the cover and includes a bottom surface and a height, whereby when the chamber is covered, the distance between the floor and the bottom surface of the at least one member is equal to the thickness of the gel strip when rehydrated. An eighth feature is that the gel carrier module may include a retaining mechanism adapted to retain the cover to the holder.

An alternative embodiment of the above aspect of the invention includes a number of features. A first feature is that the internal electrical contact points are carried by the cover and are adapted to contact the face of the gel strip with the gel strip oriented face up in the chamber. This embodiment of the invention may include a number of additional features. A second feature is that the holder includes a floor and a wall, an inner surface of the wall and upper surface of the floor define the gel strip chamber, the gel strip chamber includes a first end and a second end, the internal electrical contact point of the first electrode is carried by the cover configured to be adjacent to the first end of the gel strip chamber when the chamber is covered, the internal electrical contact point of the second electrode is carried by the cover and configured to be adjacent to the second end of the gel strip chamber when the chamber is covered. A third feature is that the cover includes a bottom surface, and the chamber includes a depth equal to the thickness of the gel strip when rehydrated so that the bottom surface of the cover maintains the gel strip in contact with the internal electrical contact points when the gel strip is rehydrated. A fourth feature is that the cover includes a sample loading reservoir. A fifth feature is that the cover includes a buffer introduction reservoir. A sixth feature is that the cover includes a bottom surface having a capillary break channel and an oil reservoir that communicates with the capillary break channel.

A third aspect of the invention involves a device for rehydrating and performing electrophoresis on a gel strip that includes a holder having a gel strip chamber configured to receive the gel strip and a rehydration buffer medium, and means for performing electrophoresis on the gel strip.

A preferred embodiment of the above aspect of the invention includes a number of features. A first feature is that the device includes means for venting electrolytic gas bubbles from the chamber. A second feature is that device includes means for introducing a test sample to the gel strip. A third feature is that the device includes means for retaining the cover to the holder. A fourth feature is that the device includes means for maintaining electrical contact between the gel strip and electrophoresis means. A fifth feature is that the device includes means for accommodating electroendosmotic flow in the gel strip during electrophoresis.

A fourth aspect of the invention involves a method of rehydrating and performing electrophoresis on a gel strip having first and second ends and a gel face. The method includes providing a device for rehydrating and performing electrophoresis on the gel strip comprising a holder including a gel strip chamber, the gel strip chamber configured to receive the gel strip and a rehydration buffer medium, and first and second electrodes having internal electrical contact points adapted to contact the gel face within the gel strip chamber near the first and second ends of the gel strip and external electrical contact points adapted to be electrically connected to a power supply for performing electrophoresis on the gel strip; providing a power supply; adding a rehydration buffer medium to the gel strip chamber; placing the gel strip into the chamber; and performing electrophoresis on the gel strip by applying voltage from the power supply to the external electrical contact points.

A preferred embodiment of the above aspect of the invention may include a number of features. A first feature is that the internal electrical contact points are adapted to contact the face of the gel strip with the gel strip oriented gel face down in the chamber, or the internal electrical contact points are adapted to contact the gel face of the gel strip with the gel strip oriented face up in the chamber. A second feature is that the gel strip may be placed into the chamber gel face down after the buffer medium is added to the rehydration chamber or gel face up before the buffer medium is added to the rehydration chamber. A third feature is that the method may include the step of providing an experimental protein sample. A fourth feature is that the chamber may include a sample introduction area between the internal electrical contact points so that the step of providing an experimental protein sample involves introducing the experimental protein sample in the sample introduction area along a lateral edge of the gel strip after the gel strip is lowered into the chamber, or alternatively, the experimental protein sample may be included in the rehydration buffer medium. A fifth feature is that the step of adding a rehydration buffer medium to the gel strip chamber occurs before placing the gel strip into the chamber, and the step of placing the gel strip into the chamber occurs before performing electrophoresis on the gel strip. A sixth feature is that the device includes a member adapted to maintain the gel strip in contact with the internal electrical contact points during electrophoresis of the gel strip. A seventh feature is that the device includes an electrolytic gas bubble escape vent that allows electrolytic gases produced at the internal electrical contact points during electrophoresis to escape. An eighth feature is that the device includes a cover for the gel strip chamber. Accordingly, the method further includes placing the cover on the gel strip chamber.

Other features and advantages of the inventions are set forth in the following detailed description and drawings, which are intended to illustrate, but not limit, the invention.

BRIEF DESCRIPTION OF THE DRAWINGS

FIG. 1 is a schematic view of an embodiment of a power application device, shown with numerous other components of an electrophoresis unit;

FIG. 2 is a perspective view of an embodiment of a gel carrier module resting on the power application device illustrated in FIG. 1;

FIG. 3 is a top plan view of the power application device illustrated in FIG. 1;

FIG. 4 is a cross-sectional view of the gel carrier module illustrated in FIG. 2;

FIG. 5 is an alternative embodiment of a power application device and a gel carrier module;

FIG. 6 is a further embodiment of a power application device and a gel carrier module;

FIG. 7 is a perspective view of an embodiment of an isoelectric focusing unit;

FIG. 8 is an exploded perspective view of an embodiment of an IPG gel strip carrier module and gel strip;

FIG. 9 is an exploded top plan view of the gel strip carrier module illustrated in FIG. 8;

FIG. 10A is a cross sectional view of the gel strip carrier module illustrated in FIG. 9, generally taken along line 10A—10A of FIG. 9, with the gel strip shown in a dry state;

FIG. 10B is a cross sectional view of the gel strip carrier module illustrated in FIG. 9, generally taken along line 10B—10B of FIG. 9, with the gel strip shown in a rehydrated state;

FIG. 11 is a perspective sectional view of the gel carrier module illustrated in FIG. 9, generally taken along line 11—11 of FIG. 9;

FIG. 12 is an exploded perspective view of an additional embodiment of a gel strip carrier module;

FIGS. 13A–13F illustrate some of the steps of a process for rehydrating a gel strip and performing isoelectric focusing on the gel strip;

FIG. 14 is an exploded perspective view of a further embodiment of a gel strip carrier module;

FIG. 15 is a bottom perspective view of the cover of the gel strip carrier module illustrated in FIG. 14;

FIG. 16A is a cross sectional view of a buffer reservoir opening and electrode in the cover illustrated in FIG. 14;

FIG. 16B is a cross sectional view of a sample loading reservoir in the cover illustrated in FIG. 14;

FIG. 16C is a cross sectional view of a pair of vents and capillary channel in the cover illustrated in FIG. 14;

FIG. 17 is a partial cross sectional view of an end portion of the gel strip carrier module illustrated in FIG. 14;

FIG. 18A is a cross sectional view of the gel strip carrier module illustrated in FIG. 14 with a dry gel strip carried therein; and FIG. 18B is a cross sectional view of the gel strip carrier module illustrated in FIG. 14 with the gel strip shown in a rehydrated state;

DETAILED DESCRIPTION OF THE PREFERRED EMBODIMENTS

An aspect of the present invention involves an improved device for applying electrical power to a gel in an electrophoresis gel carrier module. With reference to FIGS. 1–4, a preferred embodiment of a power application device, which is indicated generally by the reference numeral 100, will now be described in conjunction with a gel 102 that is carried by a gel carrier module 104. The power application device 100 allows electrophoresis gel carrier modules of various dimensions to be powered in the same electrophoresis unit without adjustment of electrical contacts or the use of conventional leads, plugs, and jacks, and provides a simpler way to make high voltage contacts.

Following a description of the power supply device 100, an exemplary embodiment of an isoelectric focusing (IEF) unit will be described in conjunction with a gel strip carrier module that carries an immobilized pH gradient (IPG) polyacrylamide gel strip. The IEF unit is a type of electrophoresis unit used for first-dimension separation of complex protein mixtures during two-dimensional electrophoresis, and incorporates a power application device similar to the power application device 100.

With reference to FIG. 3, the power application device 100 includes a power pad or platform 105 comprised of an electrically insulated support surface 106 that supports first and second electrically conductive regions or contact areas, 108, 110, respectively.

In an embodiment, the support surface 106 is substantially rectangular and is preferably made from an insulating material sold under the trademark Kapton, manufactured by the E. I. duPont company. In alternative embodiments, other insulating materials such as those used to make printed circuit boards may be used, and/or the support surface may not be rectangular.

The first electrically conductive region 108 serves as an anodic (+) contact area and the second conductive region 110 serves as a cathodic (−) contact area. Although the power pad 105 is described as having one set of two conductive regions, it will be readily understood by those skilled in the art that the power application device of the present invention may include more than one set of conductive regions. Furthermore, although the first conductive region is described as being anodic (+) and the second conductive region is described as cathodic (−), the opposite may be true.

The conductive regions 108, 110 may be plated, imprinted or otherwise adhered to the support surface 106. The conductive regions 108, 110 are preferably made of copper and include a gold coating for purposes of low resistivity and resistance to oxidation. In alternative embodiments, other conductive materials may be used such as, for example, silver, gold, copper, or other conductive materials or alloys.

The conductive regions 108, 110 may vary in size, shape, and orientation on the support surface 106. In the preferred embodiment illustrated in FIG. 3, the first conductive region 108 is generally square and has a larger area than the second conductive region 110, which is generally rectangular 112. The flat, large-surface area construction of the conductive regions 108, 110 allows electrophoresis gel carrier modules of various dimensions to be powered in the same electrophoresis unit by simply placing the gel carrier modules on the power pad 105.

It will be readily appreciated by those skilled in the art, that the size, shape, and orientation of the conductive regions 108 may vary in order to apply power to one or more gel modules having the same or different dimensions.

In an alternative embodiment of the invention, the power pad 105 may be constructed to allow for manual alteration of the configuration of the conductive regions, allow replacement of the conductive regions, and/or allow conductive regions to be added or taken from the power pad.

With reference to FIGS. 1 and 3, the conductive regions 108, 110, are electrically coupled to a power supply 120 via conductive leads 112, 114 and power cables 116, 118. The power supply 120 is preferably integrated with the power application device within an electrophoresis unit, and in communication with a computer 132 for controlling the power supplied to the conductive regions 108, 110. The first conductive region 108, i.e., anodic (+) contact area, is connected to an anodic (+) terminal of the power supply 120 and the second conductive region 110, i.e., cathodic (−) contact area, is connected to a cathodic (−) terminal of the power supply 120.

The power application device 100 preferably includes a temperature control device or temperature control mechanism 122 integrated thereto and efficient thermal contact therewith for controlling the temperature of the gel during electrophoresis. One example embodiment of a temperature control mechanism 122 is illustrated in FIG. 1. The temperature control device 122 illustrated in FIG. 1 includes a heat distribution plate 124 with cooing radiator fins 126 extending from its undersurface, and at least one solid-state Peltier heating and cooling device 128 in efficient thermal contact with the undersurface of the heat distribution plate and in communication with a computer 132. The heat distribution plate 124 is in efficient thermal contact with the power pad 105 through the insulated support surface 106, which serves as a heat transfer means. A fan (not shown) may be controlled by a computer 132 to draw air across radiator fins 126 to maintain the efficiency of the Peltier heating and cooling devices 128 when operating in cooling mode. Additionally, at least one temperature sensor 130 is in efficient thermal contact with the support surface 106, and is in communication with a computer 132. The temperature sensor 130, computer 132, and Peltier heating and cooling device 128 function work together to control the temperature of the support surface 106, and in turn, the gel, during electrophoresis in response to a selected temperature and electrophoresis voltage inputted into the computer 132 by the user.

Cooling the gel during electrophoresis is important because it allows the power application device 100 to be run at higher voltages without overheating the gel. The electrophoretic separation of a protein mixture test sample depends on the temperature of the gel during electrophoresis. Temperature control allows for uniform separations and reproducible separations. Many temperature control devices used with electrophoresis units include bulky refrigeration units that circulate a refrigerant and are located apart from the electrophoresis unit. These temperature control devices occupy large amounts of bench space in a laboratory, and may not control temperature as effectively as the present temperature control device 122.

Although a single temperature control device 122 has been described in conjunction with the power pad 105, the power pad 105 may have multiple small temperature control devices to individually control the temperature of multiple gels or multiple gel regions each at a selected different temperature during electrophoresis.

With reference to FIGS. 1, 2, and 4, the gel carrier module 104, which is constructed in accordance with an embodiment of the invention, will now be described. The gel carrier module 104, when properly positioned on the power pad 105, bridges or connects the first and second conductive regions 108, 110, respectively.

The gel carrier module 104 includes a substantially rectangular tray or holder 133 having a base 134, two substantially parallel side walls 136, and two substantially parallel end walls 138. The inside of the gel carrier module 104 comprises a gel chamber that is defined by the inner surfaces of the walls 136, 138 and an upper surface of the base 134. The gel chamber has a configuration suitable for carrying the gel 102, any applied mediums used during electrophoresis such as a buffer, test sample, or the like. The gel may be made of a number of different substances such as polyacrylamide, agarose, or the like.

The base 134 of the module 104 carries a first electrode or anodic (+) electrode 140 having a first inner electrical contact point 142 and first outer electrical contact point 144. The first inner electrical contact point 142 is located in the gel chamber and is the point or area near one end of the gel 102 where the gel directly contacts the first electrode 140 or indirectly contacts the first electrode through an appropriate conductive solution. The first outer electrical contact point 144 is located on the bottom surface of the base 134 and is the point where the first electrode 140 contacts the first conductive region or anodic (+) contact area 108.

The base 134 also carries a second electrode or cathodic electrode 146 near an opposite end of the base 134 from the first electrode 140, and includes a second inner electrical contact point 148 and a second outer electrical contact point 150. The second inner electrical contact point 148 is located in the gel chamber and is the point or area near one end of the gel 102 where the gel directly contacts the second electrode 146 or indirectly contacts the second electrode 146 through an appropriate conductive solution. The second outer electrical contact point 150 is located on the bottom surface of the base 134 and is the point where the second electrode 146 contacts the second conductive region or cathodic (−) contact area 110.

The conductive electrodes 140, 146 are preferably platinum wire or bands, or the like, which span the width of the gel chamber. The conductive electrodes 140, 146 extend beyond the side or end walls 136, 138, or through the base 134 so that internal contact point 142, 148 and external contact points 144, 150 exist.

Resting the gel carrier module 104 on the power platform 105 so that the first and second outer electrical contact points 144, 150 of the first and second electrodes 142, 146, respectively, electrically contact the first and second conductive regions 108, 110, respectively, causes an electrical connection to occur between the gel 102 and the power pad 105 suitable for performing electrophoresis on the gel 102.

The gel carrier module 104 and/or power pad 105 may include appropriate anodic (+) and/or cathodic (−) indicators for assisting the user in properly orienting the gel 102 in the module 104 and/or properly orienting the module 104 on the power pad 105 so that an appropriate electrical connection is made between the conductive regions 108, 110 of the power pad 105 and the ends of the gel 102.

Although not shown, the gel carrier module 104 may also include a cover or lid that fits with and covers the top of the module. As will become better understood below, electrical contact with the power pad can be made through such a cover.

Although not shown, the gel carrier module 104 may also include means for indicating dimensions, power requirements or limits, or other information to a sensor embedded in the support surface 106. For example, the carrier may include a magnetic or otherwise coded label that provides information to a sensor in the support surface 106. The sensor would be in communication with the computer to provide the computer with the coded information. The computer may control power, temperature, data recording, etc. based on the received information.

It is important for the support surface 106 and the opposing bottom of the base 134 of the gel carrier module 104 to be sufficiently mutually flat or non-interfering for the external contact points 144, 150 and conductive regions 108, 110 so that secure electrical contact is made between the contact points and conductive regions 108, 110. It is also important for air gaps to be minimal between the support surface 106 and the bottom surface of the gel module because the support surface serves as a heat transfer means. It is also important that the degree of contact between the external contact points 144, 150 and the respective conductive regions 108, 110 be sufficiently broad so that the requisite electrical current is carried through the gel 102 without overheating or burning of the external contact points 144, 150 or the conductive regions 108, 110.

As mentioned above, an important aspect of the power application device 100 of the present invention is that it can be used with one or more gel carrier modules having a wide variety of structural and/or electrode configurations, such as, but not limited to, the gel carrier modules described herein. If the gel module has an anode (+) electrode capable of making electrical contact with a gel it carries and the anode (+) contact area 108 of the power application device 100, and a cathode (−) electrode capable of making electrical contact with the gel it carries and the cathode (−) contact area 110 of the power application device 100, the gel carrier module will be appropriate for use with the power application device of the present invention.

Although the power application device of the present invention has been shown and described as having a generally horizontal orientation, the power application device may have other orientations such as a generally vertical orientation.

Accordingly, with reference to FIG. 5, a power application device 200 and gel carrier module 202 in accordance with an additional embodiment of the invention will now be described. The gel carrier module 202 carries a gel 204 for performing vertical electrophoresis on the gel 204. Similar to the generally horizontal power application device 100 described above, the power application device 200 includes a power pad or platform 205 comprised of an insulated support surface 206 and first and second conductive regions 208, 210, respectively. The power pad 205 is generally vertically oriented, supported by a frame (not shown), and includes a rearwardly angled portion where the second conductive region 210 resides. The angle of the rearward angled portion is greater than 90° and less than 180°, with reference to the face of most of the power pad 205. This rearwardly angled portion may be formed by bending the support surface 206 between the conductive regions 208, 210, or by forming the power platform 205 with two separate support surfaces, each carrying one of the conductive regions 208, 210, and providing the support surface carrying the second conductive region 210 at the aforementioned rearwardly inclined angle.

Similar to the power application device 100 described above, the power application device 200 illustrated in FIG. 5 preferably includes a temperature control device 222 similar to the temperature control device described above.

The gel carrier module 202 is effectively a folded version of the gel carrier module 104 described above. The gel module 202 includes a front wall 230 and a back wall 232. At a bottom portion of the walls 230, 232, the gel module 202 includes a lower buffer chamber 234 defined by a lower buffer chamber assembly 236. A first electrode 238 is carried by a lower portion of the back wall 232, and includes an inner contact point 240 and an outer contact point 242. When the gel carrier module 202 is lowered onto the power pad 205, the outer contact point 242 makes electrical contact with the first conductive region 208, i.e., anodic (+) contact area. The first electrode 238 is electrically connected with a lower surface 244 of the gel 204 through a conductive buffer 246 in the lower buffer chamber 234.

At a top portion of the walls 230, 232, the gel module 202 includes an upper buffer chamber 248 defined by an upper buffer chamber assembly 250. The back wall 232 in the upper buffer chamber assembly 250 has a rearwardly inclined angle similar to that of the power pad 205 so that the gel carrier module 202 can be supported on the power pad 205 in this area. A second electrode 252 is carried by the downwardly angled portion of the back wall 232 and includes an inner contact point 254 and an outer contact point 256. When the gel carrier module 202 is lowered onto the power pad 205, the outer contact point 256 makes electrical contact with the second conductive region 210, i.e., cathodic (−) contact area. The second electrode 252 is electrically connected with an upper surface 258 of the gel 204 through a conductive buffer 260 which fills the upper buffer chamber 248 and a sample well 262.

The electrically conductive gel 204 is contained between the vertical front wall 230 and back wall 232 in a manner familiar to those experienced in the art of vertical gel electrophoresis.

With reference to FIG. 6, a generally vertically oriented power application device 300 constructed in accordance with an additional embodiment of the invention is shown. The power application device 300 is similar to the power application device 200 described above, except the upper buffer chamber assembly of the embodiment of the gel carrier module and the upper portion of the power pad shown in FIG. 6 are not rearwardly angled as in the power application device 200 described in conjunction with FIG. 5.

The power application device 300 is used in conjunction with a gel carrier module 302. The power application device 300 is carried by a frame 305 comprising a base 306 and a vertical support 308. The base 306 includes a notch 310 in an upper surface of the base 306. A pivot clip 312 is pivotally connect to a top part of the vertical support 308 through a pin 314.

The power application device 300 includes a flat, generally vertical power pad or platform 315 that is carried by the vertical support 308. The power pad 315 includes a vertical support surface 316, and first and second conductive regions 318, 319.

The gel carrier module 302 includes a front wall 320 and a back wall 322. At a lower portion of the walls 320, 322, the gel carrier module 302 includes a lower buffer chamber 324 defined by a lower buffer chamber assembly 326. At a lower portion of the back wall 322, the back wall 322 carries a first electrode 328 having an inner contact point 330 and an outer contact point 332. A wedge-like projection 333 extends from a lower part of the lower buffer chamber assembly 326. When the gel carrier module 302 is properly positioned with the power application device 300, the outer contact point 332 of the first electrode 328 contacts the first conductive region 318 so that the first conductive region 318 is electrically coupled to a bottom surface 334 of the gel 304 through a conductive buffer 336 in the lower buffer chamber 324.

At an upper portion of the walls 320, 322, the gel carrier module 302 includes an upper buffer chamber 340 defined by an upper buffer chamber assembly 342. At an upper portion of the back wall 322, the back wall 322 carries a second electrode 344 having an inner contact point 346 and an outer contact point 348. When the gel carrier module 302 is properly positioned with the power application device 300, the outer contact point 348 of the second electrode 344 contacts the second conductive region 319 so that the second conductive region 319 is electrically coupled to a top surface 350 of the gel 304 through a conductive buffer 352 in the upper buffer chamber 340.

The gel carrier module 302 is properly positioned with the power application device 300 for vertical electrophoresis and held in this position by first inserting the wedge-like projection 333 into the notch 310 of the base 306, and then retaining the top of the gel module 302 to the top of the vertical support 308 by pivoting the pivot clip 312 over the top of the back wall 322 of the gel carrier module 302.

With reference to FIG. 7, an isoelectric focusing unit 400 constructed in accordance with a preferred embodiment of the invention will now be described. An isoelectric focusing unit 400 is a type of electrophoresis unit used for first-dimension separation of complex protein mixtures during two-dimensional electrophoresis. The isoelectric focusing unit illustrated in FIG. 7 includes a power application device 402, similar to the power application device 100 described above, for performing isoelectric focusing or separation, a type of electrophoresis, on a immobilized pH gradient (IPG) polyacrylamide gel strip 403 (FIGS. 8–11) carried by a gel carrier module 404 (FIGS. 8–11).

The isoelectric focusing unit 400 includes a generally rectangular housing 406 and a safety lid 408. The safety lid is pivotally connected to the housing 406 at a top rear part of the housing 406 for opening and closing the safety lid 408. A front part of the housing 406 includes an inclined information display area 410. Information related to rehydration and isoelectric focusing of the gel strip(s) is displayed in this area on a screen 412. The display area 410 also includes a variety of input keys 414 for inputting information to be stored in the memory of a computer such as the computer 132 described above with respect to FIG. 1. A top part of the housing 406 supports the power application device 402.

The power application device 402 includes a power pad or platform 416 comprising an insulated support surface 418 and first and second conductive regions, 420, 422, respectively. As mentioned above, the power application device 402 is similar to the power application device 100 described above in conjunction with FIGS. 1–4, and for that reason, will not be described in as much detail as above. The isoelectric focusing unit 400 can include a solid state Peltier temperature control device integrated with the power application device 402, a computer, an integrated power supply, and numerous power connections, all similar to components described above with respect to FIG. 1. The solid state Peltier temperature controller controls the temperature of the power pad 416 to a predetermined range. For example in a preferred embodiment this temperature range is 18–25° C. ±1° C. In the preferred embodiment, the power supply has 100 W of maximum power, a line voltage of 90 to 260 VAC, and delivers a voltage to the power platform 416 of 0–8000 V DC, and a current of 0 to 1.5 mA. The temperature of the gel strip(s) and the voltage supplied by the power supply is controlled via the computer in conjunction with computer software, and in response to user input, which is described in more detail below.

Similar to the gel carrier modules described above, the gel strip carrier module 404 rests on the power platform 416 for electrical connection and temperature control of the IPG gel strip 403, and includes a first electrode and a second electrode adapted to be electrically connected to the power application device 402 at the first conductive region, i.e., anodic (+) contact area, and second conductive region, i.e., cathodic (−) contact area, respectively. The power platform 416 is wide enough to accommodate up to twelve gel strip carrier modules 404. The conductive regions 420, 422 may be marked for proper placement of various lengths of gel carrier modules, e.g., include outlines 423 or end lines where different sized gel carrier modules should be positioned, and may be marked to identify the conductive regions as being anodic (+) or cathodic (−). Similarly, the gel carrier modules 404 may include some means to aid in proper placement of the gel carrier module 404 on the power pad 416 such as by including a pointed tip at the end of the module 404 near the anodic end of the gel carrier module, i.e. point is plus (+), or by anodic(+) and/or cathodic (−) end indicators.

The power platform 416 serves as an electrical connector and a thermal control system that links the gel carrier modules 404 to the programmable 8,000 V, 1.5 mA power supply and the Peltier solid state temperature controller that maintains IPG gel strip temperature at 18–25° C. ±1°. Currently available electrophoresis units were limited by a maximum rated voltage of usually $\leq$3500 V. The combination of high voltage and efficient cooling in the present invention can reduce IPG strip focusing time to as little as two to three hours, typically two to four hours.

The integrated power supply and temperature control is programmable through the input keys 414 in the display area 410, in conjunction with the computer and software for the computer. The software allows for nine isoelectric focusing programs or protocols, each at a selected temperature with nine ramp or step voltage changes to be stored by the computer. Each program may have a delayed start for isoelectric focusing so that rehydration of the gel strips 403 can occur, allowing the user to load the gel carrier modules 404 with sample in rehydration buffer in, for example, the afternoon, then have isoelectric focusing start automatically during the night. Because the isoelectric focusing requires only two to four hours for the IPG gel strips 403, the first-dimension separation can be completed, or example, overnight, by the start of the next work day. Current first-dimension isoelectric systems can take as long as two days for rehydration and isoelectric focusing. Each program may have a maximum current limit and a maximum temperature controllable by the user.

The safety lid 408 covers the entire power pad 416 to protect a user from the high voltage applied by the power pad 416 to the gel carrier module 404. For safety purposes, the isoelectric focusing unit 400 includes a high voltage shut-off device that cuts the power being supplied to the power pad 416 when the lid 408 is opened.

With reference to FIGS. 8–11, the gel strip carrier module 404, which is constructed in accordance with a preferred embodiment of the invention, will now be described. The gel carrier module 404 serves as a device for both rehydration and isoelectric focusing, a type of electrophoresis, of the immobilized pH gradient (IPG) strip 403. The length of the gel carrier module 404 can vary to accommodate IPG gel strips of various lengths.

The preferred IPG strips 403 used in conjunction with the gel carrier module 404 and IEF unit 400 are precast IPG polyacrylamide gel strips sold under the trademark Immobiline DryStrip by Amersham Pharmacia Biotech of Sweden. These strips are cast on a plastic backing 405, and are available in a variety of lengths, pH ranges, and pH gradient shapes. These IPG strips are preferred for inhibiting pH gradient distortion over time, i.e., cathodic drift, physical distortion, or breaking during handling.

The gel carrier module 404, which is in accordance with another aspect of the invention, includes an elongated, generally rectangular holder 430 and cover 432. The holder 430 is comprised of a base 434 with a flat upper, inner surface 436 and a flat lower, bottom surface 438, side walls 440 having an inner surface 442, and end walls 444 having inner surface 446. The walls 440, 444 include a flat, upper surface 447. The inner surfaces 436, 442, and 446 define a substantially rectangular gel strip chamber 448 having a depth suitable to contain a rehydrated IPG gel strip and a protective over-layer, if desired. The chamber 448 has a width and length sufficient to accomodate the width and length dimensions of the gel strip 403 to be received in the chamber 448. A first electrode 450 having an inner contact point 452, which is carried by the upper surface 436 of the base, and an outer contact point 454 (FIG. 11), which is carried by the bottom surface 434 of the base 434, is generally carried by the base 434 near an anodic (+) end of the gel carrier module 404, which, as mentioned above, may be marked or shaped to reflect such to aid the user properly orienting the gel strip 403 and/or gel module 404 during handling. A second electrode 456 having an inner contact point 458, which is carried by the upper surface 436 of the base 434, and an outer contact point (not shown, but similar to outer contact point 458), which is carried by the bottom surface 438 of the base 434, is generally carried by the base 434 near a cathodic (−) end of the gel carrier module 404, which like the anodic (+) end, may be marked or shaped to reflect such to aid the user properly orienting the strip 403 and/or the gel module 404 during handling. The electrodes 450, 456 are preferably made of platinum bands that penetrate through the bottom of the chamber 448 so that internal and external contact points or areas are made. Electrodes making internal and external contacts may be applied or constructed by means, such as, but not by way of limitation, adhesives, electrodeposition, metalization, in-place molding, or use of appropriately bent clips.

With reference to FIG. 12, an example of an alternative way to create electrodes 450, 456 having internal and external contact points is by forming the holder 430 with multiple notches 461 adjacent the electrodes 450, 456. This simplifies applying the electrodes 450, 456. After applying the electrodes 450, 456, the notches are filled with a potting compound 462 to provide a water-tight seal.

In a further alternative embodiment of the gel strip carrier module, which will be described in more detail below in conjunction with FIGS. 14–18, the electrodes making internal and external contacts may be applied through the cover of the gel carrier module.

With reference back to FIGS. 8–11, the chamber 448 of the holder 430 may be widened near the electrodes 450, 456 to form gas bubble escape or vent areas 464 for the gases created due to electrolysis of water at the electrodes 450, 456 during electrophoresis. The gas bubble escape areas 464 help to prevent the gel strip 403 from being forced off of the electrodes 450, 456 by the gas pressure created due to electrolysis of water during electrophoresis.

The inner surface 442 of the side walls 440 may include one or more sample introduction wells or areas 468 anywhere between the electrodes 450, 456. Although the present invention has been described in conjunction with a protein sample, it will be readily understood by those skilled in the art how the present invention may be applied to other samples such as DNA, RNA, amino acids, nucleic acids, and the like.

The cover 432 includes a flat bottom surface 470 that abuts a flat upper surface 447 of the walls 440, 444 to preferably seal or cover the chamber 448 when in position on the holder reasonably tight so that minimal evaporation occurs; however, the cover 432 can seal the chamber 448 liquid-tight or gas-tight. The cover may be clear so that the progress of rehydration and isoelectric focusing can be monitored visually.

With reference especially to FIGS. 10A, 10B, and 11, at least one hold-down or holding block 472 protrudes from the bottom surface 470 of the cover 432. When the cover 432 is properly positioned on the upper surface 447 of the holder 430, the holding block 472 projects into the chamber 448, leaving a distance between a bottom surface 474 of the holding block 474 and the upper surface 437 of the base 434 approximately equal to the fully rehydrated thickness of the IPG gel strip 403 when rehydrated, with its backing sheet 405 (FIG. 10B).

With reference specifically to FIG. 11, where the gel strip 403 crosses the electrode 450, 456, the gel may be slightly compressed. It is at this junction that electrolysis of water occurs, with the concomitant formation of bubbles of oxygen gas ($O_2$) and hydrogen gas ($H_2$) at the first electrode 450, i.e., anode (+), and the second electrode 456, i.e., cathode (−), respectively, during the process of electrophoresis. The pressure maintained by the cover 432 and the hold-down blocks 474 inhibits the gel strip 403 from being forced out of contact with the electrodes 450, 456 by the pressure of the gas bubbles as they evolve. The bubble escape areas 464 allow the gases to escape the electrode contact area.

In general, the gel carrier module 404 is preferably manufactured by injection molding the cover 432 of an acrylic material and molding the holder 430 of an aluminum oxide ceramic, machining the appropriate surfaces to make them flat, cut penetrations where the electrodes 450, 456 are to be provided, and then fire and braze the electrodes in place on the base 434.

With reference to FIGS. 13A–13F, a method for rehydrating and performing isoelectric focusing on the gel strip 403 using the isoelectric focusing unit 400 will now be described. The method begins by removing a protective film from the IPG gel strip 403. Next, a rehydration solution is added to the gel strip chamber 448 of the gel carrier module 404 (FIG. 13A). The rehydration solution preferably contains an experimental protein mixture sample. The entire length of the IPG gel strip 403 is then set in the rehydration solution by placing the IPG gel strip 403 in the chamber 448 of the gel module 404, gel-side facing down or gel face down (FIG. 13B). During this step, the user gently lays the IPG gel strip 403 in the gel carrier module 404, ensuring that the ends of the IPG gel strip are placed over the electrodes 450, 456, and the entire gel surface is wetted between the electrodes 450, 456. Next, if the protein sample was not included in the rehydration solution discussed above, the protein mixture sample may be applied in the sample introduction well 468 following the rehydration step (FIG. 13C). IPG cover fluid, e.g., parafin oil, may then be carefully applied along the length of the IPG gel strip to inhibit evaporation (FIG. 13D). Next, the cover 432 is seated or placed on the holder 430 (FIG. 13E). Finally, the gel carrier module 404 with gel strip 403 is properly positioned on the power pad 416 (FIG. 13F) of the isoelectric focusing unit 400, which applies a selected program of voltage steps to the electrodes 450, 456 after the IPG gel strip 403 has had sufficient time to rehydrate.

Results using the isoelectric focusing unit 400 in conjunction with the gel carrier module 404 for extracts of *E. coli* on immobilized pH gradient gel strips for two-dimensional electrophoresis were compared to results achieved using conventional commercial equipment. The equipment used for the second-dimension electrophoresis was the same for both.

The conventional equipment for the first-dimension electrophoresis consisted of an electrophoresis unit with heat exchanger sold under the name Multiphor II, IPG gel strip support module sold under the name Immobiline Dry Strip gel kit, a thermostatted circulating bath sold under the name MultiTemp III, a high voltage power supply sold under the name EPS 3500 XL, and a reswelling tray sold under the name IPG Reswelling Tray, all from Amersham Pharmacia Biotech.

After first-dimension electrophoresis, the proteins were electrophoresed off of the strip and into a vertical slab electrophoresis unit sold under the name SE 600 by Hoefer Pharmacia Biotech to perform second-dimension electrophoresis. The equipment and procedures for second-dimension electrophoresis was the same for both.

When isoelectric focusing of an additional sample of the same *E. coli* extract was performed in the gel carrier module 404, and on the isoelectric focusing unit 400, the results after vertical slab electrophoresis were virtually indistinguishable, but the rehydration and separation time was much less with the gel strip carrier module 404 and isoelectric focusing unit 400 compared to the conventional equipment.

The gel strip carrier module 404 of the present invention reduces handling of the IPG gel strips for the first-dimension electrophoresis by serving as both a rehydration and focusing chamber for an IPG strip. The gel carrier module 404 allows for the sample to be applied either through out the entire gel or in a defined zone. When the sample is included in the rehydration solution, the sample is loaded into the entire gel by absorption during the rehydration step. Alternatively, the sample introduction well 468 allows the sample to be applied in a defined zone between the electrodes 450, 456. Since the rehydrated gel is in direct contact with electrodes 450, 456 of the gel carrier module 400, the gel is in position to run without further handling. Isoelectric focusing is initiated by simply placing the gel carrier module 404, with IPG gel strip 403, rehydration solution, and sample, on the power platform or pad 416 of the power application device 402, and selecting a protocol. The computer of the isoelectric focusing unit applies power to the strip 403 automatically after a specified time for rehydration, without user intervention.

With reference to FIGS. 14–18, a gel strip carrier module 500 constructed in accordance with an additional embodiment of the invention will now be described. The gel carrier module 500 includes an elongated generally rectangular holder 502 and cover 504. The holder 502 includes one or more rectangular notches 506 along a flat bottom surface 508 for receiving one or more clips 510. The flat bottom surface 508 is necessary for making substantial uniform contact with the power pad 416. When properly positioned, each clip 510 serves as a clamping mechanism for retaining the cover 504 and holder 502 together (FIGS. 18A, 18B). The clip 510 may be a separate clip, as shown, a series of clips, or one or more clips integrated into the holder 502 and/or cover 504.

The holder 502 has a shallow, flat-bottomed recess or gel strip chamber 512 along a flat top surface 514. The gel stip chamber 512 is defined by an inner chamber wall 516 and a lower chamber surface 518. The inner wall 516 of the gel strip chamber 512 has a depth suitable to just contain the IPG gel strip 403, gel side facing up, when rehydrated on its backing sheet 405.

With reference to FIG. 15, the cover 504 has a flat bottom surface 520 which seals against the flat top surface 514 of the holder 502. The cover 504 may include a buffer reservoir opening 522 near electrode lead holes 523 (FIG. 16A), a sample loading reservoir 524 (FIG. 16B), and a capillary break channel 526 (FIG. 16C), which can optionally be filled with a light oil through a pair of vents 528. The capillary break channel 526 can serve as a capillary flow interrupter or can be filled with the light oil to prevent both capillary flow and contact with atmospheric oxygen and carbon dioxide. Without some sort of capillary break means, capillary creepage tends to occur between the flat bottom surface 520 of the cover 504 and the flat top surface 514 of the holder 502. This capillary creepage can lead to leakage, corrosion, drying and other problems.

With reference to FIG. 17, an electrical assembly for making electrical contact to the IPG gel strip 403 through the cover 504 will now be described. At positions in the cover 504 corresponding to near the ends of the gel strip chamber 512, electrode wires 530 are threaded through the electrode lead holes 523, leaving an electrode segment 532 exposed for contact with the gel or gel face of the IPG gel strip 403 when the cover 504 is properly positioned on the holder 502. An electrical circuit 533 from the electrical wires 530 continues to a metal leaf spring anchor screw 534, which retains a conductive leaf spring 535, and to ball contact 536. The anchor screw 534 is received within an anchor screw opening 538. The ball contact 536 is threadably attached to threaded fastener 540, which is received with a fastener opening 542. Electrical power is applied by the first and second conductive regions, 420, 422, of the power pad 416 to the IPG gel strip 403 through the ball contacts 536, which are located at opposite ends of the gel carrier module 500. Accordingly, the electrical circuit 533 functions as an electrode with the electrode segment 532 as an internal contact point and the ball contact 536 as an external contact point.

With reference to FIGS. 18A and 18B, the gel carrier module 500 is assembled by placing a dry IPG gel strip in the gel strip chamber 512, gel side facing up, positioning the cover 504 on the holder 502, and securing the cover 504 to the holder 502 with the clips 510 as shown. At this point the dry IPG gel strip will appear as shown in FIG. 18A. Upon addition of an appropriate volume rehydration buffer, the dry IPG gel strip 403 swells and makes contact with the electrode segment 532 (FIG. 19B). The buffer may be pipetted through the reservoir openings 524 or pipetted onto the gel face before applying the cover 504 to the holder 502. After allowing an appropriate time for full rehydration to occur, an electrical field can be applied via the power application device 402 to effect the first-dimension separation.

Solvent can be introduced and/or removed, as may be required to accommodate electroendosmotic flow during electrophoresis, through the buffer reservoir openings 522.

It will be readily apparent to those skilled in the art how some of the features described herein may be applied to other embodiments or aspects of the invention.

Although this invention has been described in terms of certain preferred embodiments, other embodiments apparent to those of ordinary skill in the art are also within the scope of this invention. Accordingly, the scope of the invention is intended to be defined only by the claims that follow.

We claim:

1. A method of rehydrating and performing electrophoresis on a gel strip having first and second ends, and a gel face, comprising:

providing a device for rehydrating and performing electrophoresis on the gel strip, the device comprising a holder including a gel strip chamber, the gel strip chamber configured to receive the gel strip and a rehydration buffer medium, and first and second electrodes having internal electrical contact points adapted to contact the gel face near the first and second ends of the gel face near the first and second ends of the gel strip within the gel strip chamber and external electrical contact points adapted to be electrically connected to a power supply for performing electrophoresis on the gel strip;

providing a power supply;

adding a rehydration buffer to the gel strip chamber;

providing an experimental protein sample;

placing the gel strip into the chamber; and performing electrophoresis on the gel strip by supplying power to the contact points, wherein the chamber includes a sample introduction area between the internal electrical contact points, the step of providing an experimental protein sample includes introducing the experimental protein sample in the sample introduction area along a lateral edge of the gel strip after the gel strip is lowered into the chamber.

2. A method of rehydrating and performing electrophoresis on a gel strip having first and second ends, and a gel face, comprising:

providing a device for rehydrating and performing electrophoresis on the gel strip, the device comprising a holder including a gel strip chamber, the gel strip chamber configured to receive the gel strip and a rehydration buffer medium, and first and second electrodes having internal electrical contact points adapted to contact the gel face near the first and second ends of the gel face near the first and second ends of the gel strip within the gel strip chamber and external electrical contact points adapted to be electrically connected to a power supply for performing electrophoresis on the gel strip;

providing a power supply;

adding a rehydration buffer to the gel strip chamber;

placing the gel strip into the chamber; and performing electrophoresis on the gel strip by supplying power to the contact points, wherein the device includes an electrolytic gas bubble escape vent that allows electrolytic gases produced at the internal electrical contact points during electrophoresis to escape.

3. A device for rehydrating and for performing electrophoresis on a gel strip having two ends and a gel face, comprising:

a holder including a gel strip chamber configured to receive the gel strip and a rehydration buffer medium; and first and second electrodes having internal electrical contact points adapted to contact the gel face near the first and second ends of the gel strip and external electrical contact points adapted to be electrically connected to a power supply for performing electrophoresis on the gel strip, wherein the holder includes an electrolytic gas bubble escape vent.

4. The device of claim 3, wherein the electrolytic gas bubble escape vent comprises widened areas in the chamber adjacent to the internal electrical contact points.

5. A device for rehydrating and for performing electrophoresis on a gel strip having two ends and a gel face, comprising:

a holder including a gel strip chamber configured to receive the gel strip and a rehydration buffer medium; and first and second electrodes having internal electrical contact points adapted to contact the gel face near the first and second ends of the gel strip and external electrical contact points adapted to be electrically connected to a power supply for performing electrophoresis on the gel strip, wherein the chamber includes a sample introduction area between the internal electrical contact points.

6. The device of claim 5, wherein the sample introduction area comprises a widened area in the chamber configured to be adjacent to a lateral edge of the gel strip.

7. A device for rehydrating and performing electrophoresis on a gel strip, comprising:

a holder including a gel strip chamber configured to receive the gel strip and a rehydration buffer medium; and means for performing electrophoresis on the gel strip, and further including means for venting electrolytic gas bubbles from the chamber.

8. A method of rehydrating and performing electrophoresis on a gel strip having first and second ends, and a gel face, comprising:

a device for rehydrating and performing electrophoresis on the gel strip, the device comprising a holder including a gel strip chamber, the gel strip chamber configured to receive the gel strip and rehydration buffer medium, and first and second electrodes having internal electrical contact points adapted to contact the gel face near the first and second ends of the gel strip within the gel strip chamber and external electrical contact points adapted to be electrically connected to a power supply for performing electrophoresis on the gel strip;

providing a power supply;

adding a rehydration buffer medium to the gel strip chamber;

providing an experimental protein sample;

placing the gel strip into the chamber; and performing electrophoresis on the gel strip by supplying power to the external electrical contact points, wherein the chamber includes a sample introduction area between the internal electrical contact points, and the step of providing an experimental protein sample involves introducing the experimental protein sample includes introducing the experimental protein sample in the sample introduction area along a lateral edge of the gel strip after the gel strip is lowered into the chamber.

9. The method of claim 8, wherein the experimental protein sample is included in the rehydration buffer medium.

10. A method of rehydrating and performing electrophoresis on a gel strip having first and second ends, and a gel face, comprising:

a device for rehydrating and performing electrophoresis on the gel strip, the device comprising a holder including a gel strip chamber, the gel strip chamber configured to receive the gel strip and rehydration buffer medium, and first and second electrodes having internal electrical contact points adapted to contact the gel face near the first and second ends of the gel strip within the gel strip chamber and external electrical contact points adapted to be electrically connected to a power supply for performing electrophoresis on the gel strip;

providing a power supply;

adding a rehydration buffer medium to the gel strip chamber;

placing the gel strip into the chamber; and performing electrophoresis on the gel strip by supplying power to the external electrical contact points, wherein the device includes an electrolytic gas bubble escape vent that allows electrolytic gases produced at the internal electrical contact points during electrophoresis to escape.

11. A device for rehydrating and for performing electrophoresis on a gel strip having two ends and a gel face, comprising:

a holder including a gel strip chamber configured to receive the gel strip and a rehydration buffer medium; and first and second electrodes having internal electrical contact points adapted to contact the gel face near the first and second ends of the gel strip and external electrical contact points adapted to be electrically connected to a power supply for performing electrophoresis on the gel strip, wherein the holder includes an electrolytic gas bubble escape vent.

12. The device of claim 11, wherein the electrolytic gas bubble escape vent comprises widened areas in the chamber adjacent to the internal electrical contact points.

13. A device for rehydrating and for performing electrophoresis on a gel strip having two ends and a gel face, comprising:

a holder including a gel strip chamber configured to receive the gel strip and a rehydration buffer medium; and first and second electrodes having internal electrical contact points adapted to contact the gel face near the first and second ends of the gel strip and external electrical contact points adapted to be electrically connected to a power supply for performing electrophoresis on the gel strip, wherein the chamber includes a sample introduction area between the internal electrical contact points.

14. The device of claim 13, wherein the sample introduction area comprises a widened area in the chamber configured to be adjacent to a lateral edge of the gel strip.

15. A device for rehydrating and performing electrophoresis on a gel strip, comprising:

a holder including a gel strip chamber configured to receive the gel strip and a rehydration buffer medium; and means for performing electrophoresis on the gel strip, further including means for venting electrolytic gas bubbles from the chamber.

* * * * *